(12) United States Patent
Shih et al.

(10) Patent No.: US 10,113,986 B2
(45) Date of Patent: Oct. 30, 2018

(54) ELECTROCHEMICAL TEST STRIP, STRIP BOARD AND METHOD FOR GENERATING THE SAME

(71) Applicant: APEX BIOTECHNOLOGY CORP., Hsinchu (TW)

(72) Inventors: Ching Yuan Shih, Hsinchu (TW); Meng Lun Lo, Hsinchu (TW); Wen Chien Jen, Hsinchu (TW); Mon Wen Yang, Hsinchu (TW)

(73) Assignee: APEX BIOTECHNOLOGY CORP., Hsinchu (TW)

( * ) Notice: Subject to any disclaimer, the term of this patent is extended or adjusted under 35 U.S.C. 154(b) by 75 days.

(21) Appl. No.: 15/215,330

(22) Filed: Jul. 20, 2016

(65) Prior Publication Data

US 2017/0023515 A1 Jan. 26, 2017

(30) Foreign Application Priority Data

Jul. 22, 2015 (TW) .............................. 104123666 A (51) Int. Cl.
*G01N 27/327* (2006.01)

(52) U.S. Cl.
CPC ..... *G01N 27/3272* (2013.01); *G01N 27/3274* (2013.01)

(58) Field of Classification Search
CPC .................................... G01N 27/327–27/3278
USPC ..... 204/403.01–403.15; 205/777.5–778, 792
See application file for complete search history.

(56) References Cited

U.S. PATENT DOCUMENTS

| | | | | |
|---|---|---|---|---|
| 2005/0224345 | A1* | 10/2005 | Taniike | G01N 33/4875 204/403.01 |
| 2006/0243589 | A1* | 11/2006 | Doi | G01N 27/3272 204/403.01 |
| 2008/0169799 | A1* | 7/2008 | Wang | G01N 27/3274 324/71.1 |
| 2009/0188791 | A1* | 7/2009 | Neubert | G01N 27/3272 204/403.01 |
| 2014/0238854 | A1* | 8/2014 | Chen | G01N 27/3272 204/403.01 |

\* cited by examiner

*Primary Examiner* — Bach T Dinh
(74) *Attorney, Agent, or Firm* — Liu & Liu (57) ABSTRACT

Provided is an electrochemical test strip, including: a sampling end disposed on a wide side of the electrochemical test strip to receive a sample; a connection end disposed on another wide side of the electrochemical test strip to connect with a measuring meter; and at least one protrusion disposed on a long side of the electrochemical test strip. A strip board and method for generating the electrochemical test strip are further provided.

11 Claims, 14 Drawing Sheets

ELECTROCHEMICAL TEST STRIP, STRIP BOARD AND METHOD FOR GENERATING THE SAME

CROSS REFERENCE TO RELATED APPLICATIONS

This Application claims priority of Taiwan Patent Application No. 104123666, filed on Jul. 22, 2015, the entirety of which is incorporated by reference herein.

BACKGROUND OF THE INVENTION

Field of the Invention

The present invention relates to electrochemical test strips, strip boards and methods for generating the same and, more particularly, to an electrochemical test strip, strip board and method for generating the same, characterized in that the electrochemical test strip has a protrusion structure externally so that it can be taken out of a test strip can easily.

Description of the Prior Art

A conventional electrochemical test strip consists of an insulating substrate, an electrode unit, a reaction layer, a lower adhesive layer, a lower spacer, an upper adhesive layer and an upper spacer. Generating electrochemical test strips involves forming multiple electrode units on an insulating substrate board, stacking components, such as mother boards each having the aforesaid layers, and cutting the insulating substrate board by a pressing process (like die stamping) to form separate electrochemical test strips. The pressing process removes unwanted waste from between the electrochemical test strips. In recent years, a clearance-free blanking device is developed and launched to reduce a waste ratio with a clearance-free intertwined grid punch die. However, all the layers of the electrochemical test strips generated by the aforesaid technique, except the electrode units and the reaction layers, are adhered together by an adhesive. The adhesive is exposed from the electrochemical test strips readily as a result of compression while the pressing process is underway.

At this point in time, if the electrochemical test strips generated by a conventional pressing molding technique are placed inside a test strip can, the exposure of the adhesive from the electrochemical test strips will cause the electrochemical test strips to adhere together, thereby rendering it difficult to separate the electrochemical test strips and using them. Accordingly, it is important to provide a novel inventive technique for solving the problem.

SUMMARY OF THE INVENTION

Results of research carried out by the inventor of the present invention are described below. During a manufacturing process of electrochemical test strip a punching die exerts a force downward, or both upward and downward, to perform a cutting process; meanwhile, adhesive layers of the electrochemical test strips are simultaneously impacted by the punching die and compressed by components mounted on the other layers. As a result, adhesive of the adhesive layers is likely to be squeezed out. Eventually, when packed in a can, the electrochemical test strips adhere to each other because of the squeeze-out. Take a strip-like electrochemical test strip as an example, the squeeze-out usually happens to two long sides, rather than two wide sides, of the electrochemical test strip. The two wide sides of the electrochemical test strip usually have a sampling end and a connection end. Although the sampling end and the connection end are subjected to substantially the same impact given by the punching die as the other parts of the electrochemical test strip, to enable the electrochemical test strip to electrically connect with a measuring meter, the adhesive layer, lower spacer and upper spacer of the electrochemical test strip seldom cover part of an electrode unit, and therefore the connection end of the electrochemical test strip is free of any adhesive layer at the cutting point, thereby precluding squeeze-out. The sampling end usually has a hollow-cored space that serves as a reaction zone. The hollow-cored space functions as a buffer that reduces the impact of the punching die on the sampling end and the compression of components mounted on each layer of the test strip, and in consequence squeeze-out of the sampling end is insignificant. Conversely, unlike the sampling end and the connection end, the two long sides of the electrochemical test strip provide the main adhesion points which, when impacted by the punching die, cause the adhesive layer to flow over the two long sides, when compressed by the adhesive layer itself, an insulating substrate, a lower insulating plate and an upper insulating plate.

In view of the aforesaid and other problems, the present invention provides solutions described below.

According to an embodiment, the present invention provides an electrochemical test strip, comprising: a sampling end disposed on a wide side of the electrochemical test strip to receive a sample; a connection end disposed on another wide side of the electrochemical test strip to connect with a measuring meter; and at least one first protrusion disposed on a first long side of the electrochemical test strip.

According to an embodiment of the present invention, the electrochemical test strip is characterized in that the first long side has at least one recess.

According to an embodiment of the present invention, the electrochemical test strip is characterized in that the recess are directly connected to the at least one first protrusion.

According to an embodiment of the present invention, the electrochemical test strip is characterized in that the at least one first protrusion is disposed between the two recesses.

According to an embodiment of the present invention, the electrochemical test strip further comprises at least one second protrusion disposed on a second long side of the electrochemical test strip, wherein the second long side differs from the first long side.

According to an embodiment of the present invention, the electrochemical test strip is characterized in that the at least one first protrusion has a largest protrusion width parallel to the first long side, wherein a ratio of a length of the first long side after a length of the connection end has been subtracted therefrom to the largest protrusion width ranges from 100:1 to 25:1.

According to an embodiment of the present invention, the electrochemical test strip is characterized in that the at least one first protrusion has a largest projecting height perpendicular to the first long side, and the largest projecting height ranges from 0.02 mm to 1 mm, from 0.06 mm to 0.8 mm, or from 0.1 mm to 0.5 mm.

According to an embodiment of the present invention, the electrochemical test strip further comprises an insulating substrate covered with an electrode unit; a spacer; and an adhesive layer for adhering the electrode unit and the insulating substrate to the spacer, wherein the adhesive layer has adhesion strength greater than 1.5 kg/ln, preferably greater than 5 kg/ln.

According to an embodiment of the present invention, a strip board for forming the electrochemical test strips comprises the electrochemical test strips and an insulating board waste for connecting the electrochemical test strips to each other.

According to an embodiment of the present invention, any two adjacent ones of the electrochemical test strips of the strip board are separated by a distance of 3 to 10 mm.

According to an embodiment, the present invention provides a method for generating the electrochemical test strip, comprising: providing the strip board; and cutting the strip board with a pressing die such that the electrochemical test strips each separate from the insulating substrate waste, wherein the at least one first protrusion of the electrochemical test strips is still connected to the insulating substrate waste.

The present invention still includes the other aspects whose features and advantages are defined by the appended claims, illustrated with preferred embodiments and described below.

DETAILED DESCRIPTION OF THE EMBODIMENTS

To enable persons skilled in the art to fully understand the present invention and the appended claims, the preferred embodiments of the present invention are depicted by accompanying drawings. To focus on the essential technical features of the present invention, the description below might not cover convenient elements, related materials, and their related treatment techniques. Similar elements shown in the accompanying drawings are denoted by identical reference numerals. To present the present invention clearly, the accompanying drawings are not drawn to scale. The devices and elements described in the preferred embodiments below are illustrative rather than restrictive of the scope of the present invention.

Figure 1:
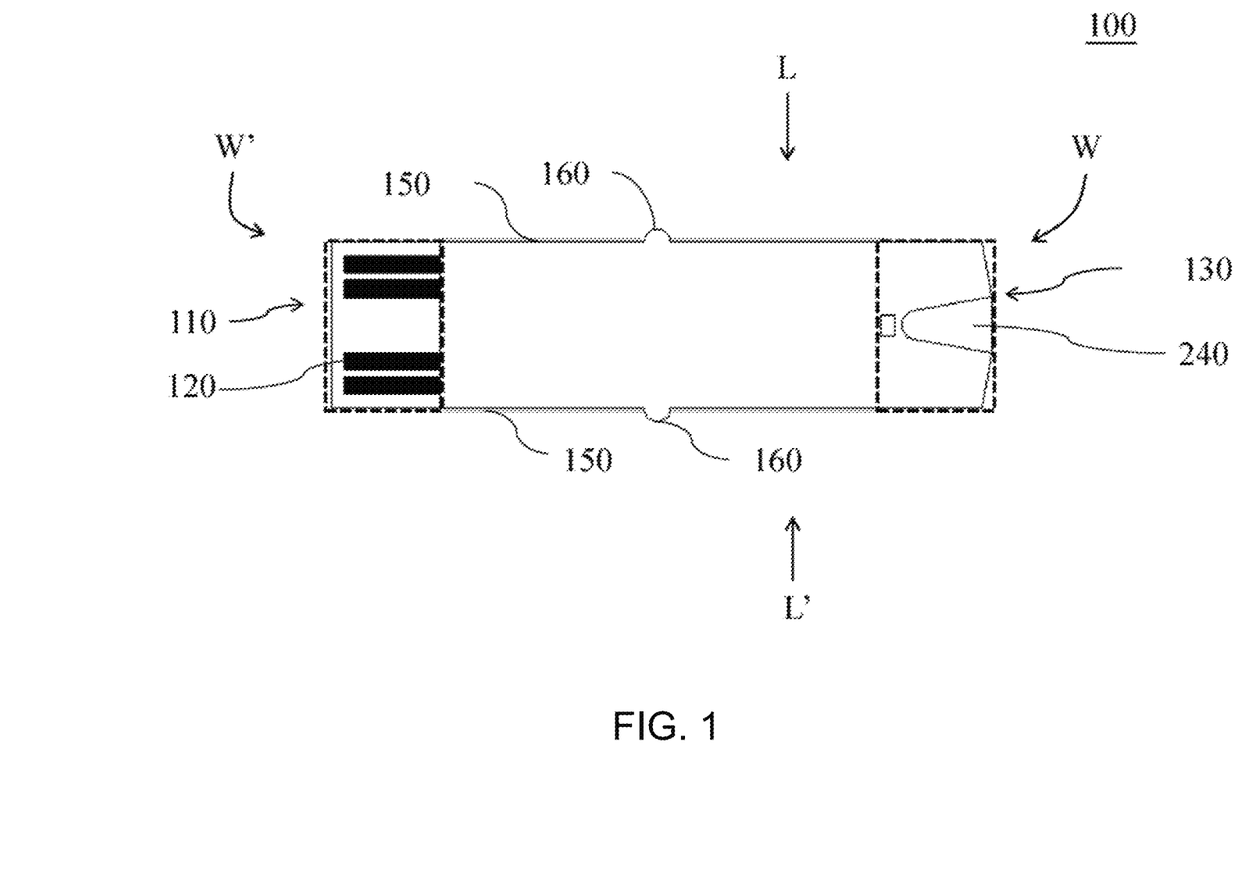
FIG. 1 is a schematic view of an electrochemical test strip according to a first embodiment of the present invention.

FIG. 1 is a schematic view of an electrochemical test strip 100 according to a first embodiment of the present invention. In this embodiment, the electrochemical test strip 100 looks like a strip. In another embodiment, the electrochemical test strip takes on any appropriate shape. Referring to FIG. 1, the electrochemical test strip 100 comprises a sampling end 130, a connection end 110, and at least one first protrusion 160. The sampling end 130 is disposed on a wide side W of the electrochemical test strip 100 to receive a sample under test. The connection end 110 is disposed on another wide side W of the electrochemical test strip 100 to connect with a measuring meter (not shown). The at least one first protrusion 160 is disposed on a first long side L and a second long side L' of the electrochemical test strip 100, respectively. In this embodiment, the first long side L and the second long side L' each have only one first protrusion 160. In another embodiment, the first long side L and the second long side L' each have multiple protrusions. In yet another embodiment, the first long side L is equal to or different from the second long side L' in the quantity of protrusions. According to an embodiment of the present invention, either the first long side L or the second long side L' lacks any protrusion.

Figure 2:
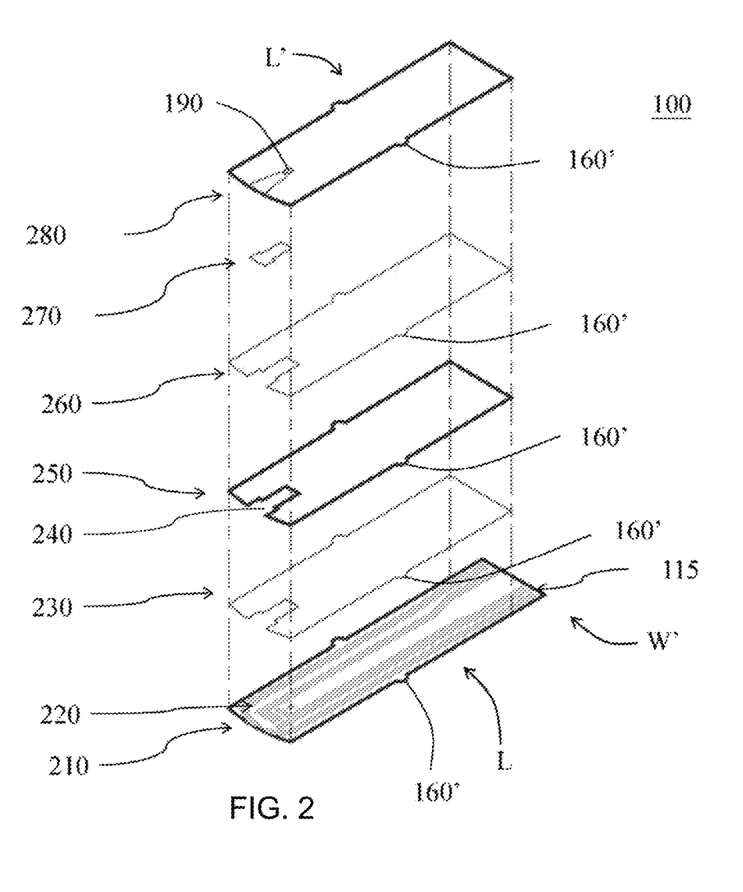
FIG. 2 is an exploded schematic view of the electrochemical test strip according to the first embodiment of the present invention.

FIG. 2 is an exploded schematic view of the electrochemical test strip 100 according to the first embodiment of the present invention. The electrochemical test strip 100 comprises an insulating substrate 210, an electrode unit 220, a lower adhesive layer 230, a lower spacer 250, an upper adhesive layer 260, a reaction layer 270 and an upper spacer 280. The insulating substrate 210 is made of polyvinyl chloride (PVC), fiberglass (FR-4), polyester sulfone, bakelite, polyethylene terephthalate (PET), polycarbonate (PC), polypropylene (PP), polyethylene (PE), polystyrene (PS), glass plate, ceramic, a combination thereof, or any other appropriate material. Referring to FIG. 2, the electrode unit 220 is disposed on the insulating substrate 210. The electrode unit 220 of the electrochemical test strip 100 comprises at least two electrodes which are insulated from each other. The electrode unit 220 is made of any electrically conductive material, such as palladium paste, platinum paste, gold paste, titanium paste, carbon paste, silver paste, copper paste, gold silver mixture paste, carbon silver mixture paste, or any combination thereof. Referring to FIG. 2, the lower adhesive layer 230, lower spacer 250, upper adhesive layer 260, and upper spacer 280 together forms a hollow-cored space that serves as a reaction zone 240. The lower spacer 250 covers a portion of the electrode unit 220, and another portion of the electrode unit 220 exposes the reaction zone 240 at the sampling end 130 and the connection end 110. A sample under test (for example, blood) enters the reaction zone 240 to undergo an electrochemical reaction subsequently. The reaction layer 270 comprises at least one active substance and electrically conductive medium for undergoing a chemical reaction with the sample under test.

Referring to FIG. 2, the lower adhesive layer 230 is disposed between the lower spacer 250 and the insulating substrate 210. The lower adhesive layer 230 is made of a material which exhibits high pliability, high resistance to heat, and high pressing precision to enable the insulating substrate 210 and the lower spacer 250 to adhere together. The lower adhesive layer 230 is made of a material that includes but is not limited to polyvinyl chloride (PVC) insulating adhesive, ethylene terephthalate insulating adhesive, thermally dried insulating varnish or UV curable insulating varnish. However, the present invention is not restrictive of the materials which the lower adhesive layer 230 is made of, as the lower adhesive layer 230 of the present invention can be made of any material and work, provided that the lower spacer 250 and the insulating substrate 210 adhere together tightly, wherein the adhesive layer has adhesion strength greater than 1.5 kg/ln, or preferably greater than 5 kg/ln. The upper spacer 280 covers the lower spacer 250, a portion of the electrode unit 220 and a portion of the insulating substrate 210. The upper adhesive layer 260 is disposed between the upper spacer 280 and the lower spacer 250 to enable the upper spacer 280 and the lower spacer 250 to adhere together. The upper adhesive layer 260 is made of the same material as the lower adhesive layer 230.

Figure 4:
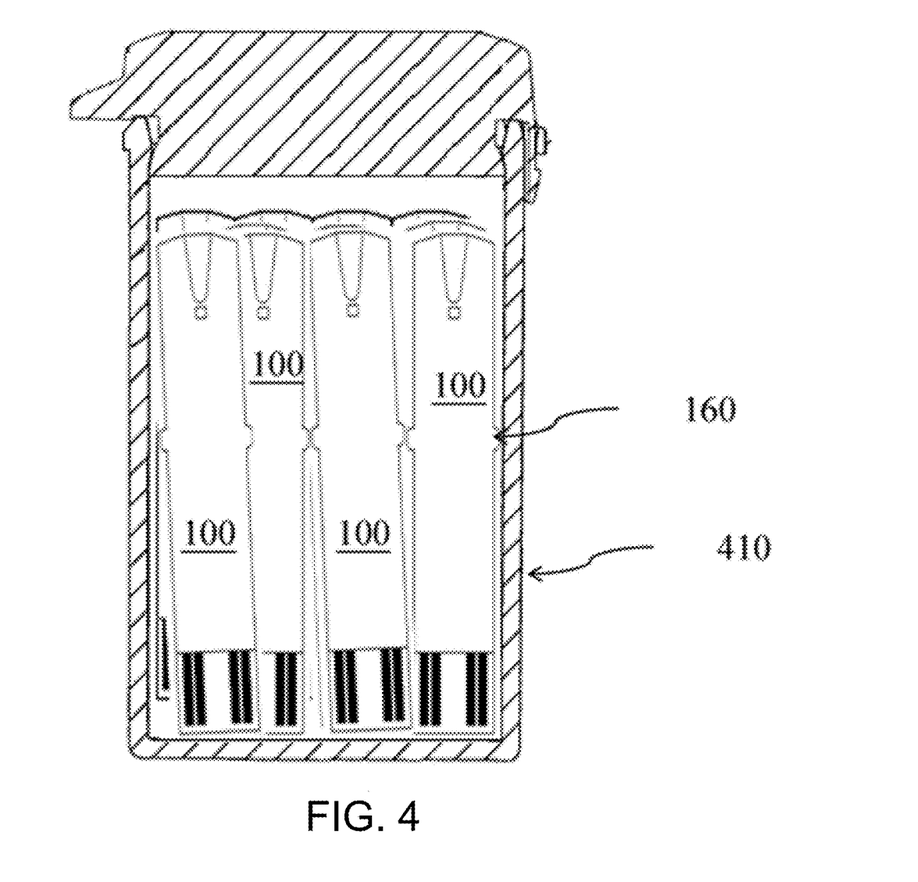
FIG. 4 is a cross-sectional view of a test strip can loaded with the electrochemical test strips according to a third embodiment of the present invention.
Figure 11:
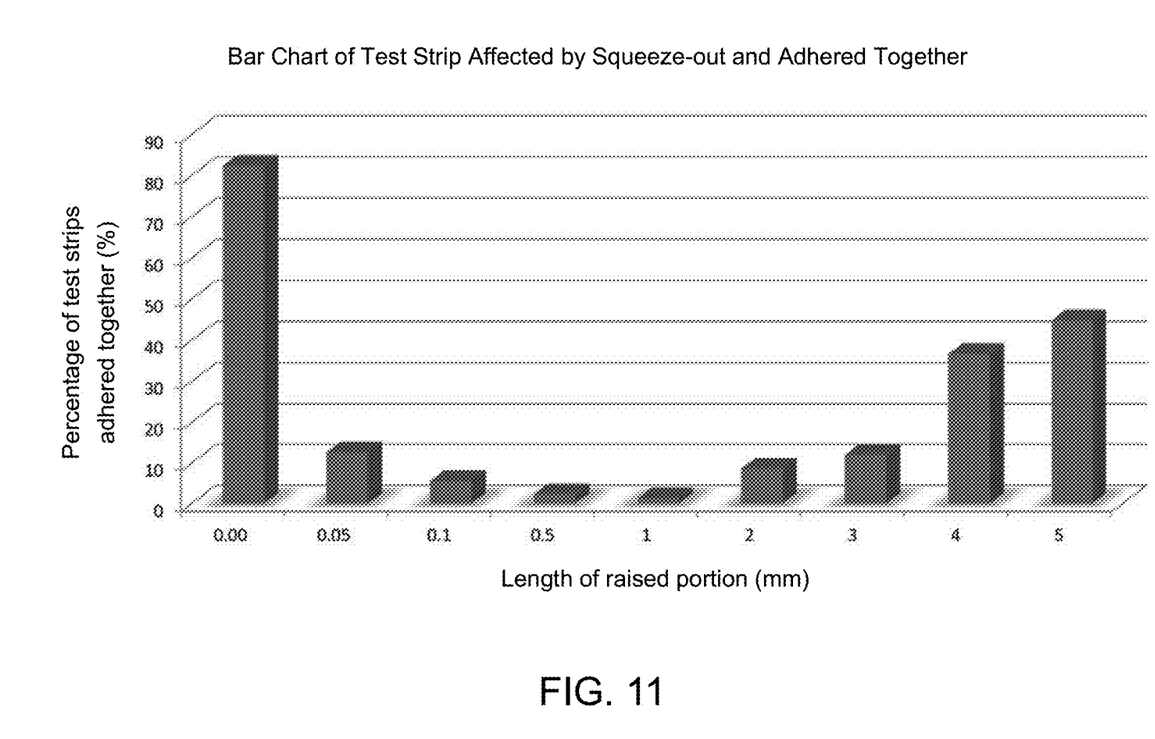
FIG. 11 is a bar chart of test strip squeeze-out.

Referring to FIG. 1 and FIG. 2, a vent 190 is disposed on the electrochemical test strip 100 to discharge a gas from the reaction layer 270. According to the present invention, the sampling end 130 of the electrochemical test strip 100 extends from the wide side W to the vent 190, whereas the connection end 110 of the electrochemical test strip 100 extends from the wide side W but is not covered by the lower adhesive layer 230 and/or the lower adhesive layer 260. As described before, a squeeze-out is likely to occur on the two long sides of the electrochemical test strip 100, for example, at a squeeze-out point 150 shown in FIG. 1. Hence, in this embodiment of the present invention, the at least one protrusion 160 is disposed on the first long side L and the second long side L' of the electrochemical test strip 100 each. Due to the at least one protrusion 160, the lateral surface (thickness surface) of the electrochemical test strip 100 is uneven wherever it corresponds in position to the first long side L (the second long side L') and thus is impacted by the punching die unevenly, so as to mitigate compression and reduce the squeeze-out. Therefore, the chance that a squeeze-out will occur to the electrochemical test strips 100 produced from the same batch of test strip board is greatly reduced. Furthermore, the at least one protrusion 160 reduces the contact area between the electrochemical test strips 100 or the contact area between each electrochemical test strip 100 and the test strip can (as shown in FIG. 4) so that the adhesion is effectively precluded. Referring to FIG. 1, preferably, the at least one protrusion 160 is located at the middle point of the first long side L (the second long side L'). Referring to FIG. 2, preferably, the at least one protrusion 160 comprises sub-protrusions 160' of components of the aforesaid layers. The protrusions of the present invention reduce the possible contact area between the test strips and thus prevent the test strips from adhering to each other as a result of a squeeze-out; hence, an overly large ratio (i.e., a large protrusion) of the protrusion at the test strip end allows the protrusion to provide an adhesion point to the test strip, whereas an overly small protrusion fails to reduce contact area. Referring to FIG. 11, there is shown a bar chart of the probability of adhesion which occurs to test strips in a test strip can, wherein the long side L of the test strips is 34 mm long, and protrusions thereof vary in length.

Figure 3:
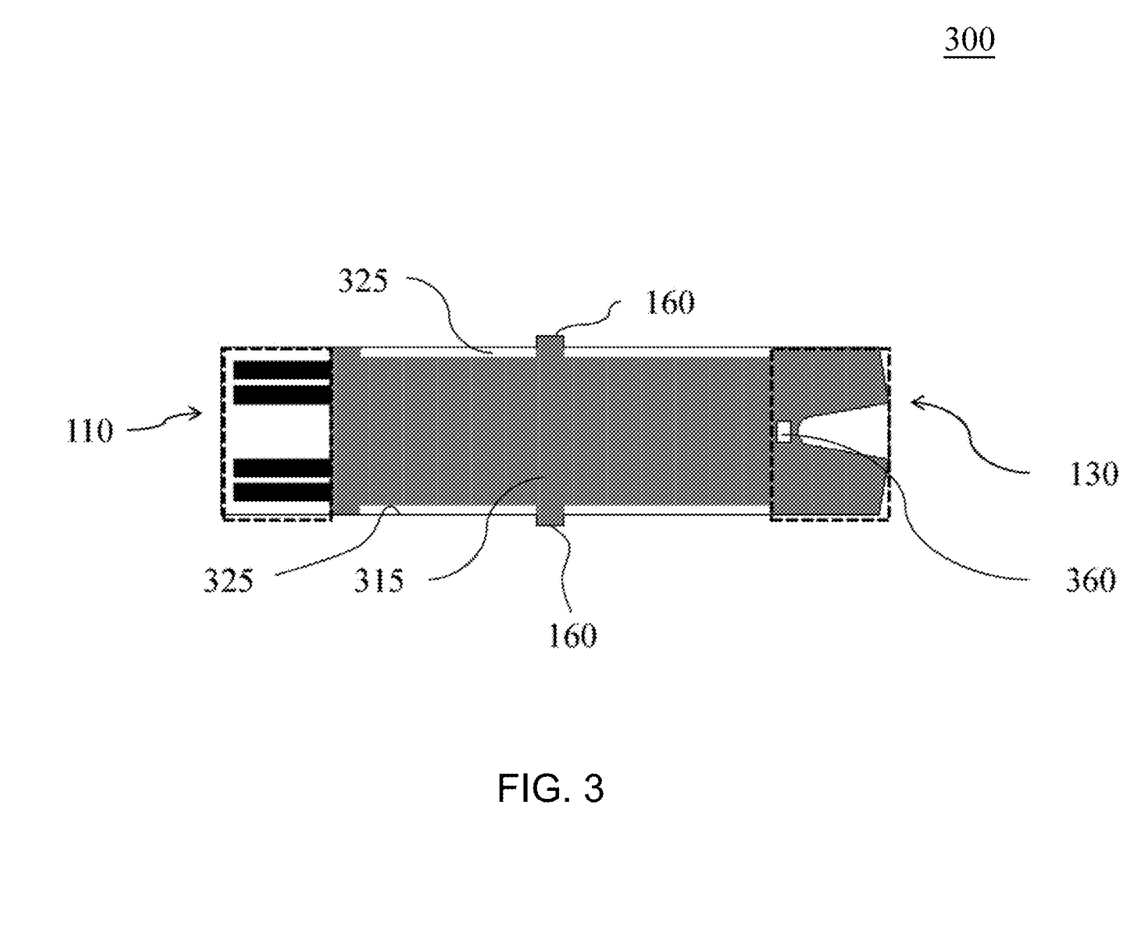
FIG. 3 is a schematic view of an electrochemical test strip according to a second embodiment of the present invention.

FIG. 3 is a schematic view of an electrochemical test strip 300 according to a second embodiment of the present invention. As shown in the diagram, the second embodiment is distinguished from the first embodiment by technical features as follows: in the second embodiment, the first long side L of the electrochemical test strip 300 has the at least one protrusion 160 and at least one recess 325, preferably two recesses 325, wherein the at least one protrusion 160 is disposed between the two recesses 325. In a variant embodiment, the recesses 325 of the first long side L are in the number of one, two or more. As shown in the diagram, in the second embodiment, compared with the at least one protrusion 160, the recesses 325 preferably take up more area of the lateral surface (thickness surface) of the electrochemical test strip 300 on the first long side L. Preferably, the recesses 325 are directly connected to the at least one protrusion 160. Preferably, the recesses 325 do not extend to the sampling end 130 and the connection end 110. In the second embodiment, the second long side L of the electrochemical test strip 300 also has two recesses 325 with technical features described above. In a variant embodiment, the recesses 325 on the two long sides are, or are not, equal in quantity. In the second embodiment, the recesses 325 preferably comprise sub-recesses (not shown) of components of the aforesaid layers.

In the second embodiment, the electrochemical test strip 300 is intended to further reduce the chance that a squeeze-out will occur on the long sides. In the second embodiment, the upper and lower adhesive layers 260, 230 are processed before the components of the aforesaid layers are stacked, to not only cut out the reaction zone 240 but also cut out the recesses 325. Advantages of the second embodiment are as follows: the insulating substrate 210, the lower spacer 250 and the upper spacer 280 are further fixed in place by the adhesive layers at the at least one protrusion 160; and the recesses 325 mitigate impacts and compression and thus are effective in preventing a squeeze-out.

FIG. 4 is a cross-sectional view of a test strip can 410 loaded with the electrochemical test strips 100 according to a third embodiment of the present invention. As shown in FIG. 4, since the at least one protrusion 160 is disposed on the two long sides L and L' of the electrochemical test strips 100, the contact area between the electrochemical test strips 100 or between each electrochemical test strip 100 and a test strip can (not shown) is reduced, and therefore the two long sides L and L' of the electrochemical test strips 100 are effectively prevented from having the electrochemical test strips 100 adhering to each other or to the test strip can 410 as a result of a squeeze-out. Therefore, users can take a single electrochemical test strip 100 out of the test strip can 410 easily.

Figure 5:
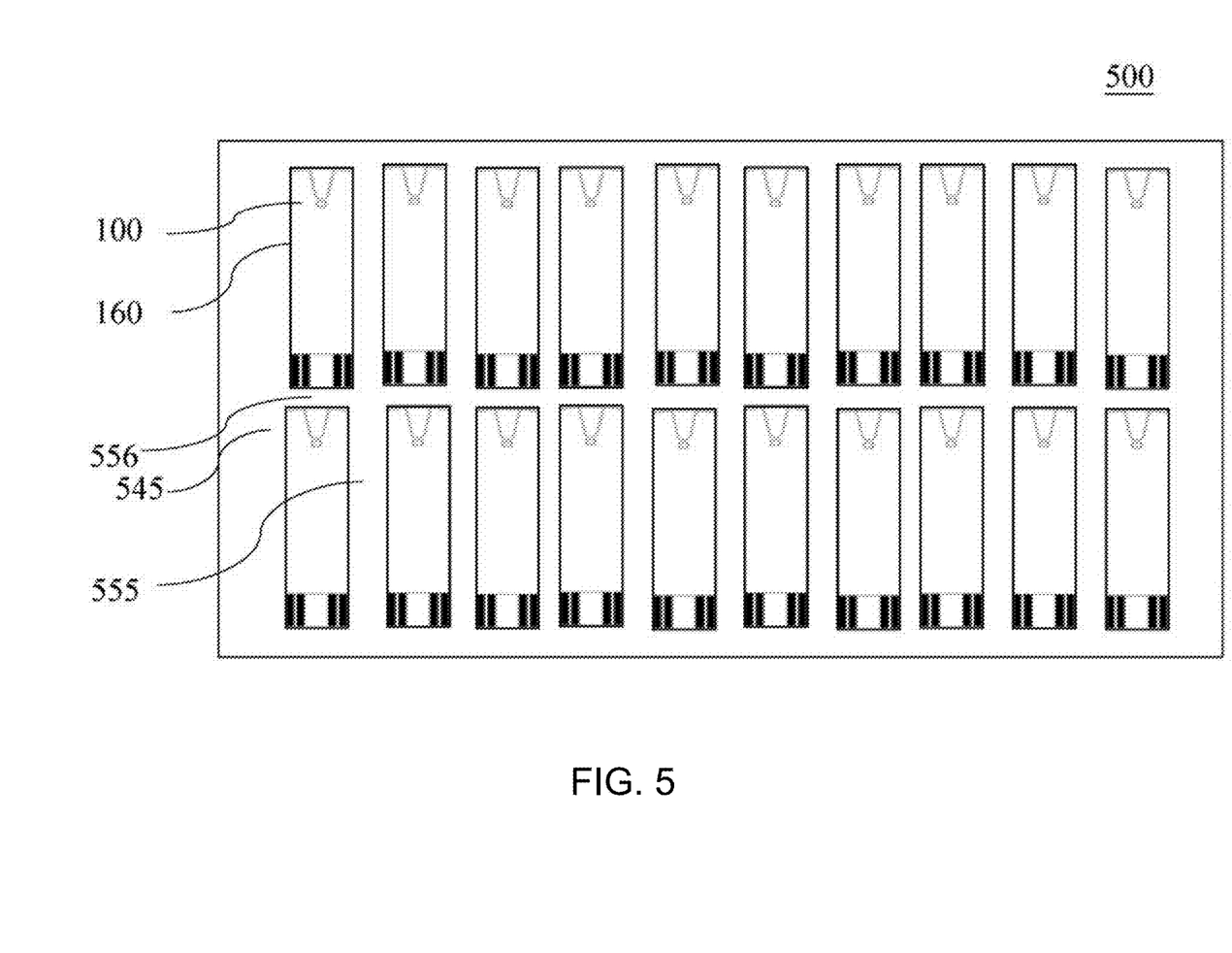
FIG. 5 is a schematic view of a strip board for use in a manufacturing process of the electrochemical test strip according to a fourth embodiment of the present invention.
Figure 10:
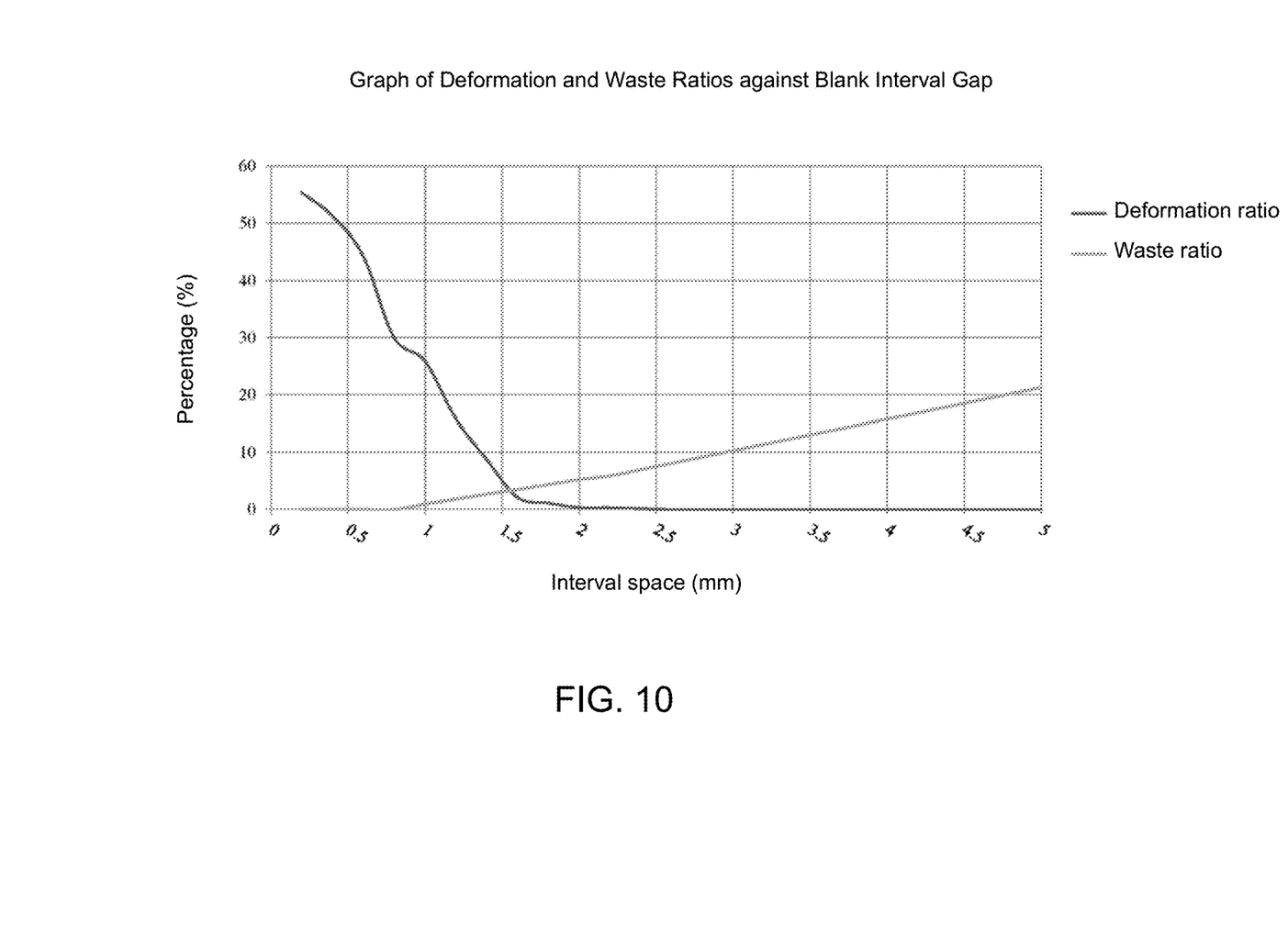
FIG. 10 is a graph of board insulation clearance deformation and waste ratio.

FIG. 5 is a schematic view of a strip board 500 for use in a manufacturing process of the electrochemical test strips 100 according to a fourth embodiment of the present invention. The electrochemical test strips 100 are arranged on the strip board 500 in an end-to-end paired manner. To ensure that a punching die in operation will have sufficient room for required movement and thereby avoid damaging the punching die itself and the electrochemical test strips 100, any two adjacent electrochemical test strips 100 are separated by the distance 556 perpendicular to the wide sides, and any two adjacent electrochemical test strips 100 are separated by the distance 555 perpendicular to the long sides. Preferably, the distance 555/556 ranges from 3 mm to 10 mm. Given the distance 555/556, the strip board 500 has a board waste 545. Before the strip board 500 is cut, the board waste 545 enables the electrochemical test strips 100 to connect with each other. The distance 555 or 556 allows for the least clearance of the punching die. If the distance 555 or 556 is less than 2 mm, the electrochemical test strips 100 being excessively impacted by the punching die will crack or deform for a lack of a buffer space. In view of this, the manufacturing process usually requires a buffer space of 2 mm. If the distance 555 or 556 is larger than 5 mm, the waste rate will be 20% or more, thereby causing unnecessary waste, as shown in FIG. 10.

Figure 6A:
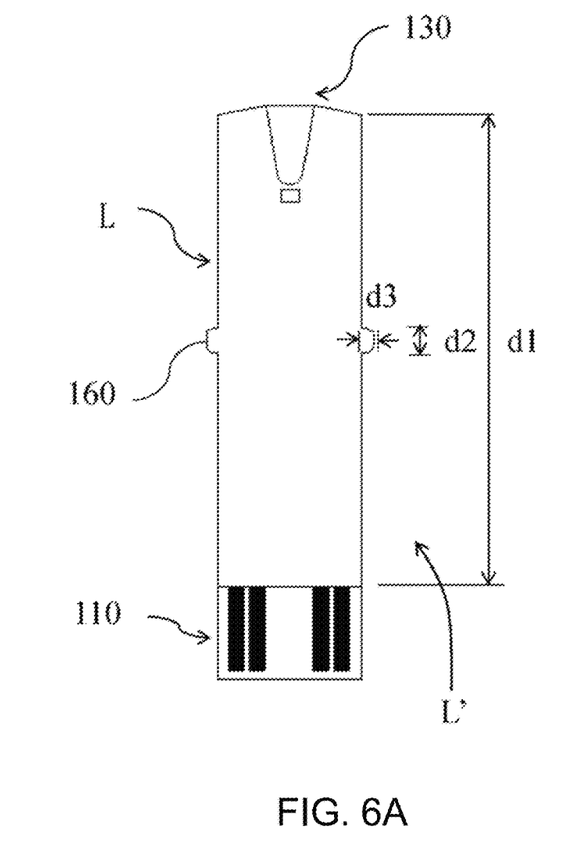
FIG. 6A through FIG. 6F are schematic views of the electrochemical test strips according to a fifth embodiment of the present invention.
Figure 6B:
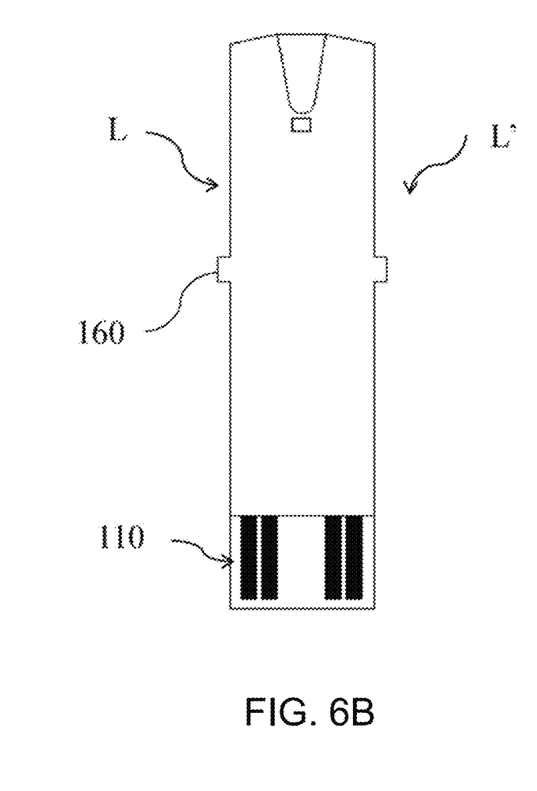
Figure 6C:
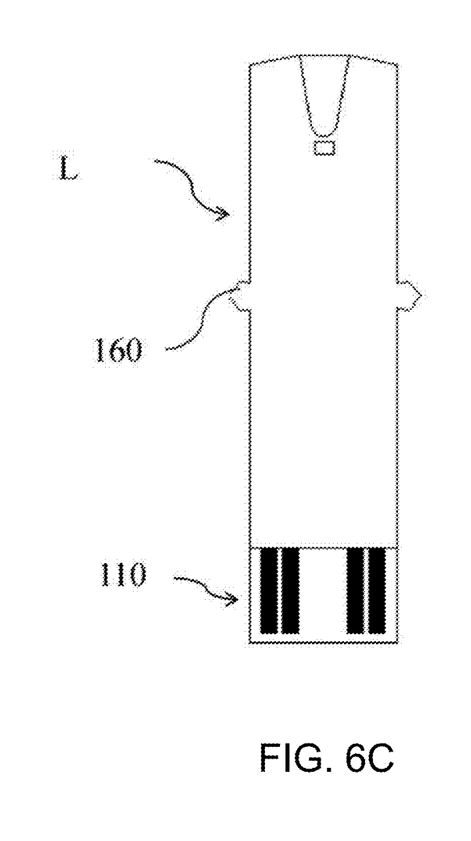
Figure 6D:
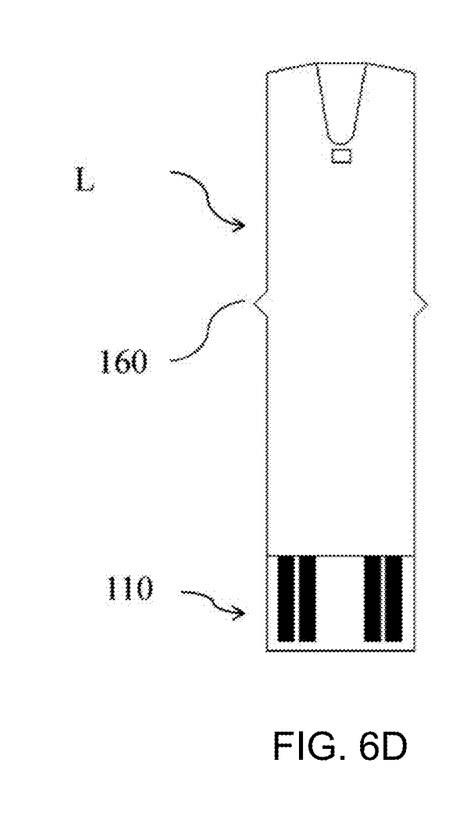
Figure 6E:
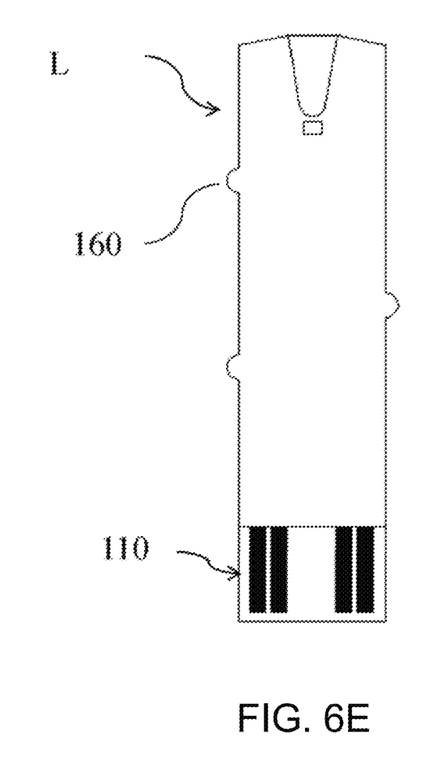
Figure 6F:
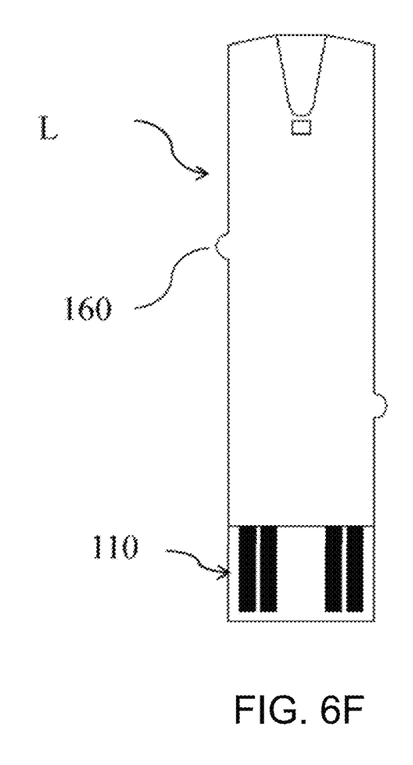

FIG. 6A through FIG. 6F are schematic views of the electrochemical test strips according to a fifth embodiment of the present invention. As shown in the diagrams, the electrochemical test strips each have the connection end 110, the sampling end 130 and the two long sides L and L' which the at least one protrusion 160 is disposed on. As shown in FIG. 6A through FIG. 6F, the at least one protrusion 160 is of any appropriate shape. The quantity of the at least one protrusion 160 and the position of the at least one protrusion 160 on the two long sides L and L' are subject to changes, including multiple protrusions 160 shown in FIG. 6E, and the at least one protrusion 160 disposed asymmetrically on the two long sides L and L' shown in FIG. 6F. According to the present invention, the at least one protrusion 160 is sized to achieve a required function. Referring to FIG. 6A, the protrusion 160 has a largest protrusion width d2 which is parallel to the long side L or L'. A length d1 is equal to a length of the long side L or L' minus a length of the connection end 110. The ratio of the length d1 to the protrusion width d2 of the protrusion 160 ranges from 100:1 to 25:1, or equals to 100:1 or less, preferably equals to 50:1 or less, and most preferably equals to 25:1 or less. The protrusion 160 has a largest protrusion height d3 perpendicular to the long side L or L'. The largest protrusion height d3 ranges from 0.02 mm to 1 mm, preferably from 0.06 mm to 0.8 mm, and most preferably from 0.1 mm to 0.5 mm.

Figure 7:
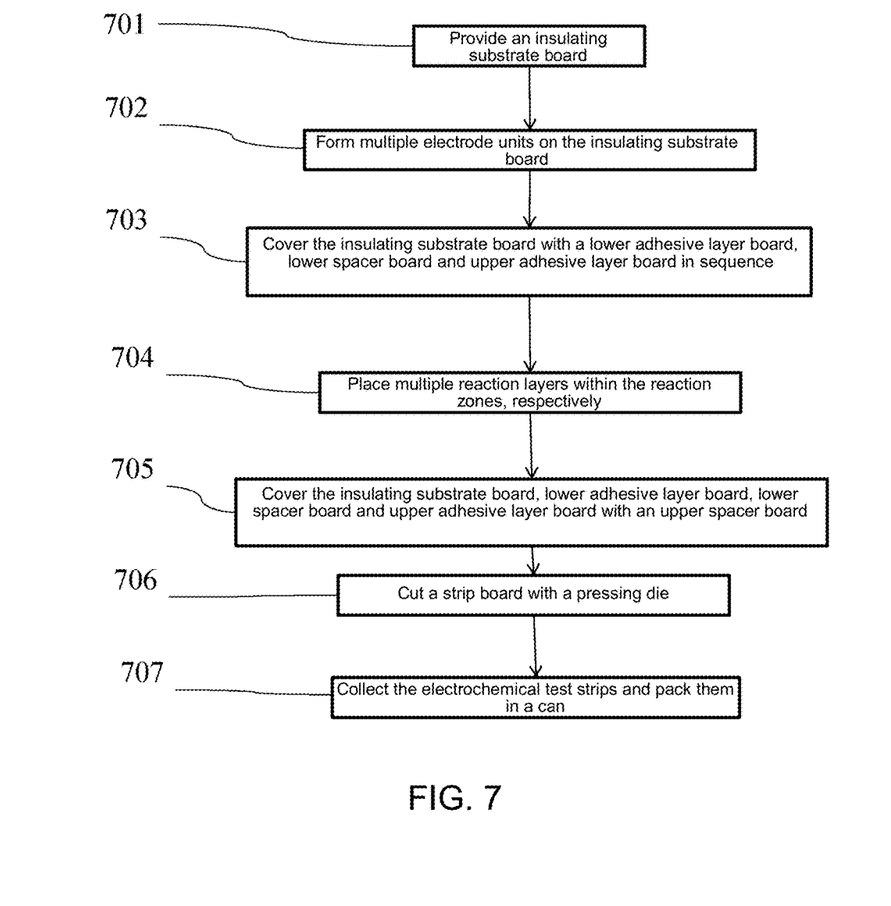
FIG. 7 is a flowchart of a method for generating the electrochemical test strip according to a sixth embodiment of the present invention.

FIG. 7 is a flowchart of a method for generating the electrochemical test strip 100 according to a sixth embodiment of the present invention. The sixth embodiment can be understood with reference to FIG. 1, FIG. 2, FIG. 5 and FIG. 7. Step 701 involves providing an insulating substrate board. Step 702 involves forming multiple electrode units on the insulating substrate board, with each electrode unit corresponding to an electrochemical test strip, wherein the test strips are spaced apart by an appropriate gap. The method for forming the electrodes units includes but is not limited to etching, laser, and printing. Step 703 involves covering the insulating substrate board with a lower adhesive layer board, lower spacer board and upper adhesive layer board in sequence, wherein the lower adhesive layer board, lower spacer board and upper adhesive layer board are already cut to take on a required shape, for example, and thus form multiple reaction zones, respectively, which correspond in position to the sampling ends of the electrode units, respectively, wherein also formed beforehand are multiple holes corresponding in position to the connection ends of the electrode units, respectively. Step 704 involves placing multiple reaction layers within the reaction zones, respectively. Step 705 involves covering the insulating substrate board, lower adhesive layer board, lower spacer board and upper adhesive layer board with an upper spacer board. The lower spacer board forms, beforehand, required elements, such as the reaction zones and ventilation openings. Components of all the layers on the insulating substrate board are adhered to each other tightly by an appropriate technique, such as pressing, baking or UV irradiation, to accomplish the strip board 500 shown in FIG. 5. As mentioned before, any two adjacent ones of the electrochemical test strips are separated by a distance 555/556 which ranges from 3 mm to 10 mm.

Step 706 involves cutting a strip board with a pressing die so that the electrochemical test strips each separate from an insulating substrate waste. In this embodiment, after the cutting process has been finished, the protrusions of the electrochemical test strips are still connected to the insulating substrate waste, and thus the electrochemical test strips do not completely separate from the insulating substrate waste. Hence, the electrochemical test strips and the insulating substrate waste do not fall onto a punching machine to cause a mechanical failure or an unnecessary waste of resources. The pressing die has multiple protrusions which correspond in cutter shape to the positions of the protrusions of the electrochemical test strips, respectively. After the pressing and cutting processes have been finished, due to the geometric shape of their protrusions, the electrochemical test strips exhibit a bayonet effect to thereby connect with the insulating substrate waste. After the electrochemical test strips and the insulating substrate waste have exited the punching machine, the electrochemical test strips are separated, completely and one by one, from the insulating substrate waste in an appropriate manner, for example, manually. Finally, step 707 involves collecting the electrochemical test strips and packing them in a can. The strip board which has been cut with the punching machine will have a flat smooth surface, if the two long strip ends are free of any protrusion; meanwhile, the strip board (waste) exerts a force only on the periphery of the test strips. Furthermore, when undergoing a pressing and cutting process, the test strips have already separated slightly from the strip board under an impact, and thus the test strips fall onto a punching machine readily, thereby prolong the production process (because workers have to remove the fallen test strips) and causing a mechanical failure (because the test strips fall onto gears.) According to the present invention, the raised portions increase the test strips' area which the strip board (waste) exerts a force on. Furthermore, the geometric shape of protrusions brings into full play a bayonet function (in a way like how a jigsaw puzzle gets connected by a bayonet) to thereby effectively reduce the chance that the test strips will fall onto the punching machine. However, the protrusion height affects the bayonet function and waste ratio. A large protrusion height is accompanied by an increase in the waste rate. A small protrusion height precludes the bayonet effect and reduces the function otherwise brought by adhering two test strips together. Moreover, the raised portions overlap a gap space to reduce the waste rate.

Figure 8:
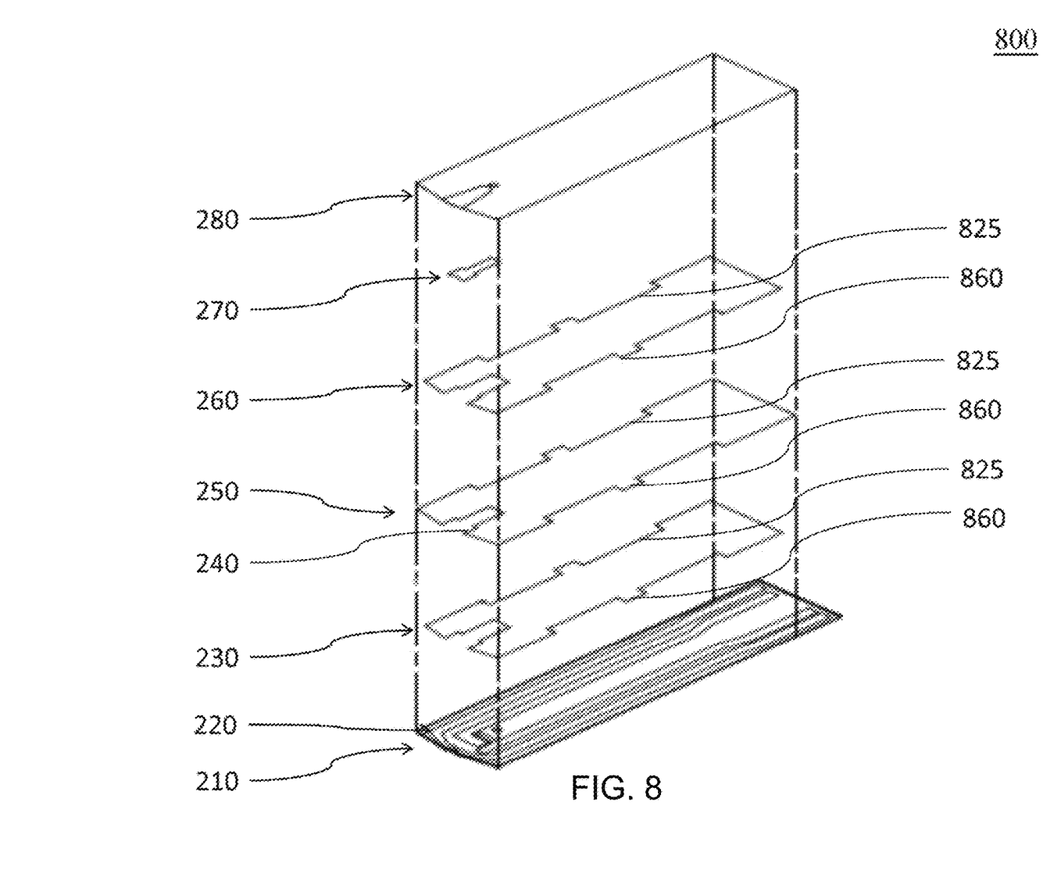
FIG. 8 is an exploded schematic view of the electrochemical test strip according to a seventh embodiment of the present invention.
Figure 9:
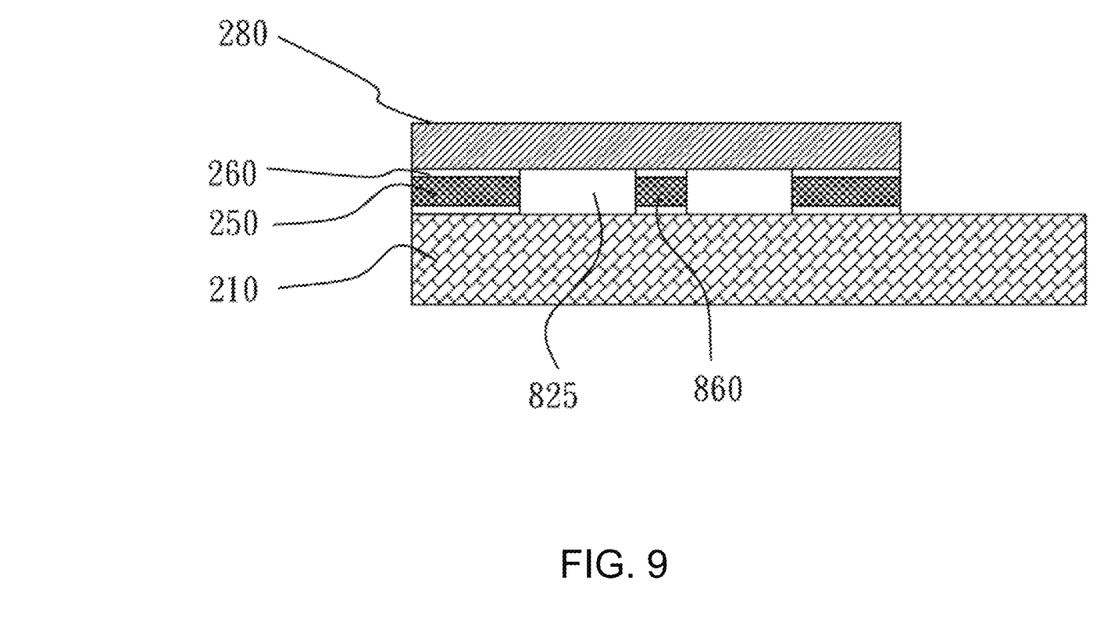
FIG. 9 is an exploded schematic view of the electrochemical test strip according to the seventh embodiment of the present invention.
Figure 12:
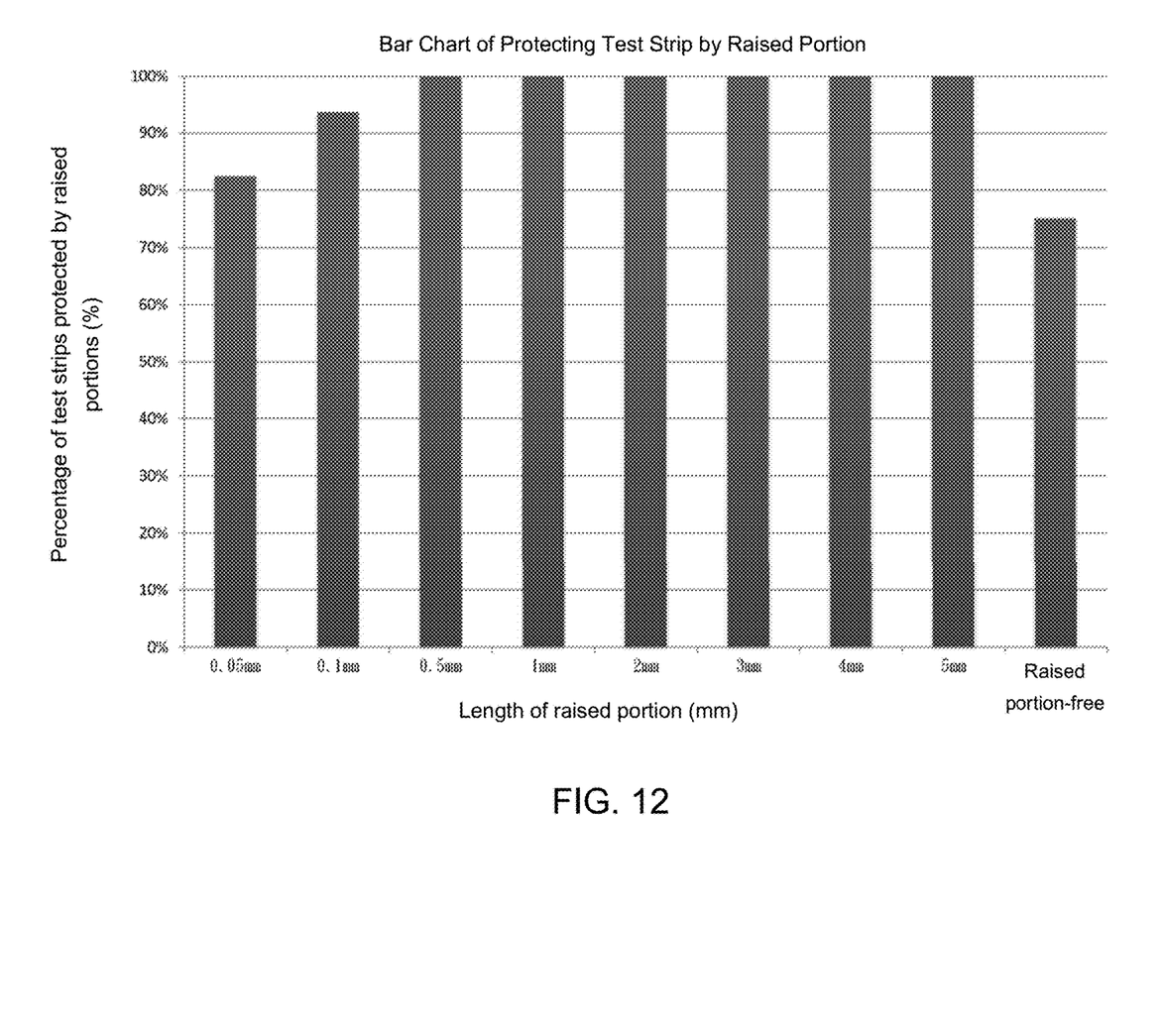
FIG. 12 is a bar chart of protection provided by a raised portion for test strips.

FIG. 8 is an exploded schematic view of the electrochemical test strip according to a seventh embodiment of the present invention. In this embodiment, the electrochemical test strip comprises an insulating substrate 210, an electrode unit 220, a lower adhesive layer 230, a lower spacer 250, an upper adhesive layer 260, a reaction layer 270 and an upper spacer 280. Referring to FIG. 8 and FIG. 9, the lower adhesive layer 230 and the upper adhesive layer 260 are attached to a surface of the lower spacer 250 beforehand, and the lower spacer 250 forms the reaction zones 240, depressed portions 825 and raised portions 860 by pressing molding. Then, the lower adhesive layer 230 is adhered to the insulating substrate 210, whereas the upper adhesive layer 260 is adhered to the upper spacer 280. Therefore, the electrochemical test strip has at least one depressed portion 825 on the first long side L and the second long side L' each. The raised portion 860 is centrally disposed at the depressed portion 825. The raised portion 860 supports the parts of the insulating substrate 210 and the upper spacer 280 corresponding in position to the depressed portion 825 so that a hollow-cored resilient space is formed on the lateral surface (thickness surface) of an electrochemical test strip 800 and corresponds in position to the first long side L (second long side L'). As soon as the punching die exerts an impact on the electrochemical test strip, the hollow-cored resilient space mitigates the impact and provides a receiving space for a squeeze-out which will otherwise reach the margin of the electrochemical test strip, thereby solving squeeze-out problems effectively. In the seventh embodiment, the raised portion 860 supports the parts of the insulating substrate 210 and the upper spacer 280 corresponding in position to the depressed portion 825. If the raised portion 860 has an overly large width, it will reduce the space provided by the depressed portion 825 and adapted to contain the squeeze-out and the capability of the hollow-cored resilient space to mitigate the impact (through the hollow-cored structure of the depressed portion 825). If the raised portion 860 has an overly small width, it will fail to support the insulating substrate 210 and the upper spacer 280, and in consequence the electrochemical test strip 800 will be damaged by the punching machine while being processed with the punching machine for lack of sufficient supporting points. A statistic analysis of test strip protection rate is performed on electrochemical test strips with the long side L of a length of 34 mm and the raised portions 860 of different lengths. Referring to the bar chart of FIG. 12, the length of the raised portion 860 accounts for 15% (5 mm), more preferably 5% (1.7 mm), and most preferably 1% (0.34), of the length of the long side L.

The present invention can be embodied in any other specific way without departing from the spirit or required features of the present invention. Every aspect of the aforesaid preferred embodiments of the present invention must be regarded as illustrative rather than restrictive. Therefore, the scope of the present invention is defined by the appended claims as opposed to the aforesaid description. All changes made to the aforesaid preferred embodiments and equivalent meanings, which fall within the scope of the present invention, must be deemed falling within the claims of the present invention.

What is claimed is:

1. An electrochemical test strip, comprising:
    a sampling end disposed on a wide side of the electrochemical test strip to receive a sample;
    a connection end disposed on another wide side of the electrochemical test strip to connect with a measuring meter; and
    at least one first protrusion disposed on a first long side of the electrochemical test strip,
    wherein the first long side is longer than each of the wide side and the another wide side,
    wherein the at least one first protrusion has a largest protrusion width d2 parallel to the first long side, a length d1 is equal to a length of the first long side minus a length of the connection end, and a ratio of the length d1 to the largest protrusion width d2 is between 100:1 and 25:1,
    wherein the first long side has at least two recesses and the at least one first protrusion is disposed between the at least two recesses.

2. The electrochemical test strip of claim 1, wherein the at least two recesses are directly connected to the at least one first protrusion.

3. The electrochemical test strip of claim 1, further comprising at least one second protrusion disposed on a second long side of the electrochemical test strip, wherein the second long side differs from the first long side.

4. The electrochemical test strip of claim 1, wherein the at least one first protrusion has a largest projecting height perpendicular to the first long side, and the largest projecting height ranges from 0.02 mm to 1 mm.

5. The electrochemical test strip of claim 1, further comprising:
    an insulating substrate covered with an electrode unit;
    a spacer; and
    an adhesive layer for adhering the electrode unit and the insulating substrate to the spacer, wherein the adhesive layer has adhesion strength greater than 1.5 kg/In, or greater than 5 kg/In.

6. A strip board for forming the electrochemical test strip of claim 1, comprising the electrochemical test strips and an insulating board waste for connecting the electrochemical test strips to each other.

7. The strip board of claim 6, wherein any two adjacent ones of the electrochemical test strips are separated by a distance of 3 mm to 10 mm.

8. A method for generating a test strip, comprising the steps of:
    providing the strip board of claim 6; and
    cutting the strip board with a pressing die such that the electrochemical test strips each separate from the insulating substrate waste, wherein the at least one first protrusion of the electrochemical test strips is still connected to the insulating substrate waste.

9. The electrochemical test strip of claim 1, wherein the at least one first protrusion has a largest projecting height perpendicular to the first long side, and the largest projecting height ranges from 0.06 mm to 0.8 mm.

10. The electrochemical test strip of claim 1, wherein the at least one first protrusion has a largest projecting height perpendicular to the first long side, and the largest projecting height ranges from 0.1 mm to 0.5 mm.

11. The electrochemical test strip of claim 1, wherein a terminal of the at least one first protrusion is in alignment with a side of the sampling end along the first long side.

* * * * *